United States Patent
Izume

(10) Patent No.: US 9,962,978 B2
(45) Date of Patent: May 8, 2018

(54) CAN PRINTING APPARATUS

(71) Applicant: I. MER CO., LTD., Kyoto-shi (JP)

(72) Inventor: Masayuki Izume, Kyoto (JP)

(73) Assignee: I. MER CO., LTD., Kyoto-Shi (JP)

( * ) Notice: Subject to any disclaimer, the term of this patent is extended or adjusted under 35 U.S.C. 154(b) by 0 days. days.

(21) Appl. No.: 15/327,035

(22) PCT Filed: Jul. 28, 2015

(86) PCT No.: PCT/JP2015/071311
§ 371 (c)(1),
(2) Date: Jan. 18, 2017

(87) PCT Pub. No.: WO2016/017610
PCT Pub. Date: Feb. 4, 2016

(65) Prior Publication Data
US 2017/0157964 A1 Jun. 8, 2017

(30) Foreign Application Priority Data
Jul. 31, 2014 (JP) .................................. 2014-155802

(51) Int. Cl.
*B41M 5/00* (2006.01)
*B41F 33/00* (2006.01)
(Continued)

(52) U.S. Cl.
CPC ........... *B41M 5/0088* (2013.01); *B41F 17/22* (2013.01); *B41F 19/007* (2013.01);
(Continued)

(58) Field of Classification Search
CPC .... B41M 5/0088; B41M 1/40; B41F 33/0036; B41F 19/007; B41F 17/22; B41J 3/42; B41J 3/44; B41J 3/4073
See application file for complete search history.

(56) References Cited

U.S. PATENT DOCUMENTS 8,899,718 B2 * 12/2014 Yamada ................... B41M 1/04
347/101
2001/0054364 A1 12/2001 Kusaka
(Continued)

FOREIGN PATENT DOCUMENTS

EP 2100733 9/2009
JP 05-126762 5/1993
(Continued)

OTHER PUBLICATIONS

International Search Report for corresponding International Application No. PCT/JP2015/071311, dated Oct. 20, 2015.
(Continued)

*Primary Examiner* — Julian Huffman
(74) *Attorney, Agent, or Firm* — Mori & Ward, LLP

(57) ABSTRACT

A can printing apparatus 1 includes a main printer 2 having plural plate cylinders 47 for printing different colors and performing printing onto side surfaces of cans, a secondary printer 6 performing additional printing to the side surfaces of the cans after the printing by the main printer, and a can inspection machine 5 inspecting a printing state. The can inspection machine 5 includes a can rotation device 51 which rotates cans C, a can imaging device 52 which takes images of the cans C and an image processing device 53 which processes the taken images, and the secondary printer 6 includes a printing head 6a which faces a side surface of a can held by the can rotation device 51 of the can inspection machine 5 and a processing unit which gives an instruction of printing to the printing head 6a based on a predetermined printing pattern and processing data of the image processing device 53 of the can inspection machine 5.

3 Claims, 11 Drawing Sheets

(51) Int. Cl.
  *B41F 19/00*  (2006.01)
  *B41F 17/22*  (2006.01)
  *B41M 1/40*  (2006.01)
  *B41J 3/44*   (2006.01)
  *B41J 3/407*  (2006.01)
  *B41J 3/42*   (2006.01)

(52) U.S. Cl.
  CPC ......... *B41F 33/0036* (2013.01); *B41J 3/4073* (2013.01); *B41J 3/42* (2013.01); *B41J 3/44* (2013.01); *B41M 1/40* (2013.01)

(56) References Cited

U.S. PATENT DOCUMENTS

| | | |
|---|---|---|
| 2006/0137548 A1 | 6/2006 | Vetter |
| 2011/0067584 A1 | 3/2011 | Mueller et al. |
| 2015/0174917 A1 | 6/2015 | Noll et al. |

FOREIGN PATENT DOCUMENTS

| | | |
|---|---|---|
| JP | 05120412 A1 * | 5/1993 |
| JP | 2002-1923 | 1/2002 |
| JP | 2004-251855 | 9/2004 |
| JP | 2011-230797 | 11/2011 |
| JP | 2012-86870 | 5/2012 |
| JP | 2013-544675 | 12/2013 |
| JP | 2015-063021 | 4/2015 |
| WO | WO 03/106177 | 12/2003 |
| WO | WO 2012/053406 | 4/2012 |
| WO | WO 2012/054655 | 4/2012 |
| WO | WO 2013/182454 | 12/2013 |

OTHER PUBLICATIONS

Extended European Search Report for corresponding EP Application No. 15826944.9-1019, dated Feb. 2, 2018.

* cited by examiner

CAN PRINTING APPARATUS

TECHNICAL FIELD

The present invention relates to a can printing apparatus, and more specifically relates to a can printing apparatus having a can inspection machine which inspects a printing state.

BACKGROUND ART

As a printing apparatus for cans, there is known a printing apparatus including a plate-type printer (main printer) having plural plate cylinders for printing different colors and performing printing on side surfaces of cans and an inkjet printer (secondary printer) performing additional printing on side surfaces of cans after the printing by the main printer (Patent Literature 1).

As a can inspection machine which inspects the printing state of cans, there is disclosed a can inspection machine including a can rotation device which rotates cans, a can imaging device which takes images of rotating cans and an image processing device which processes the taken images in Patent Literature 2. In the Patent Literature 2, the image processing device has an image inspection means for inspecting whether printing is correctly performed as compared with a master image, and lack of printing, stains on appearance and so on are inspected by the image inspection means. When using the can inspection machine, the unmanned operation is realized and the cost can be reduced.

CITATION LIST

Patent Literature

Patent Literature 1: JP-A 2012-86870
Patent Literature 2: JP-A 5-126762

SUMMARY OF INVENTION

Technical Problem

The printing apparatus disclosed in Patent literature 1 has an advantage that an added value in printing onto cans is increased by performing additional printing by the secondary printer, while the printing apparatus has a problem that the addition of the secondary printer costs a lot.

An object of the present invention is to provide a can printing apparatus capable of realizing the unmanned operation and performing additional printing at low cost by using the can inspection machine.

Solution to Problem

A can printing apparatus according to the present invention includes a main printer having plural plate cylinders for printing different colors and performing printing onto side surfaces of cans, a can inspection machine for inspecting a printing state, and a secondary printer performing additional printing to the side surfaces of the cans after the printing by the main printer, in which the can inspection machine has a can rotation device which rotates cans, a can imaging device which takes images of the side surfaces of the cans and an image processing device which processes the taken images, and the secondary printer has a printing head which faces a side surface of a can held by the can rotation device of the can inspection machine and a processing unit which gives an instruction of printing to the printing head based on a predetermined printing pattern and processing data of the image processing device of the can inspection machine.

The secondary printer is a plateless type printer, for example, an inkjet type printer. The inkjet printer has a quick dry property, which can perform printing of arbitrary patterns by preparing information on the computer's side. Accordingly, various kinds of printing can be performed by allowing the head thereof to face side surfaces of cans and by giving printing instructions. Here, it is necessary to determine at which place on the surface of the can the printing is performed when performing printing by the secondary printer.

The can inspection machine has the can rotation device, the can imaging device and the image processing device, inspecting the printing state, in which a position where the inspection of the can is started is measured with high accuracy. The position where the printing is performed by the secondary printer can be specified by using the can inspection machine. Accordingly, additional printing can be performed at adequate positions on the side surface of the can.

The can inspection machine is used as described above, thereby realizing the unmanned operation and performing additional printing at low cost.

The can imaging device may include a first camera for taking an image of the entire can, a second camera for taking an image of an end portion of an opening side of the can. It is preferable that the image processing device has an image inspection means for inspecting whether the image is correctly printed as compared with a master image by using the image taken by the first camera, a density measurement means for measuring densities in positions designated by respective colors by using the image taken by the first camera, and a printing deviation value measurement means for measuring deviation values with respect to set positions of marks for inspecting printing deviation printed on the end portion of the opening side of the can for respective colors by using the image taken by the second camera.

The first camera has been used from the past for performing image inspection, and the image inspection and the density measurement can be executed by using the first camera. The second camera may image only the end portions of the opening side of the cans.

In the inspection by the image inspection means, the master image is compared with the taken image pixel by pixel, and a partial lack in the image, stains by ink scattering and so on are inspected.

In the inspection by the density measurement means, densities in places designated by respective colors (density measurement places) are measured. The density measurement results are fed back to the main printer, thereby correcting the density before a density defective product is produced and maintaining good printing state.

Marks for inspecting printing deviation values are printed on the end portion of the opening side of the can for respective colors, which are imaged by the second camera and printing deviation values are calculated by the printing deviation value measurement means. The printing deviation value measurement results are fed back to the main printer, thereby correcting (registering) printing deviation values (positional deviation of plate cylinders of the main printer) before a printing deviation defective product is produced and maintaining the good printing state.

The can rotation device preferably includes a vertical drive-side rotation shaft driven by a motor, a vertical driven-side rotation shaft which rotates integrally with the drive-side rotation shaft, a cylindrical holding member concentrically attached to the driven-side rotation shaft and adsorbing and holding the can and an encoder which detects the rotation of the drive-side rotation shaft, in which the drive-side rotation shaft is opposite to the driven-side rotation shaft in the axial direction in a state of being positioned in the vertical direction, and it is preferable that the drive-side rotation shaft and the driven-side rotation shaft integrally rotate by providing magnets exerting the attraction force to each other in a lower end of the drive-side rotation shaft and in an upper end of the driven-side rotation shaft.

It is necessary to provide the can rotation device which accurately rotates the can once at the time of taking images. In the above can rotation device, the drive-side rotation shaft and the driven-side rotation shaft integrally rotate by the attraction force exerted between magnets, thereby accurately rotates the can once. A slight gap may exist between the drive-side rotation shaft and the driven-side rotation shaft, however, it is preferable that there is no gap for increasing the attraction force.

The printing deviation value measurement results calculated by the printing deviation value measurement means are fed back to the main printer, and positions of plate cylinders are automatically adjusted by a registering device based on the printing deviation value measurement results. Accordingly, the printing deviation values (positional deviations of plate cylinders of the main printer) can be corrected (registered) before a printing deviation defective product is produced, and the good printing state can be maintained. Accordingly, the printing deviation value measurement results in the can inspection machine are immediately fed back to the main printer, which prevents production of a printing deviation defective product and corrects the printing deviation before the printing deviation defective product is produced.

It is preferable that respective plate cylinders of the main printer print marks for inspection used for detecting printing deviation values of respective plate cylinders on the end portion of the opening side of the can.

The end portion of the opening side of the can is a portion to be covered with a lid, which is a place where the printing is not performed and the inspection is not required in the conventional cans. In the printing apparatus according to the present invention, marks for inspecting printing deviation values for respective colors are printed on the end portion of the opening side of the can. The marks for inspecting printing deviation values are not seen by being covered with the lid, and the can is all the same as the conventional one on appearance in a state where the can is filled with a beverage as a product.

The marks for inspecting printing deviation values are imaged by the camera provided in the can inspection machine. The camera for inspecting printing deviation values is provided separately from the camera for inspecting images which is used from the past.

Advantageous Effects of Invention

In the can printing apparatus according to the present invention, it is possible to measure densities and printing deviation values necessary for improving the printing accuracy of the main printer by the can inspecting machine which inspects the printing state, and additional printing can be performed by using the can rotation device and the image processing device of the can inspection machine, thereby performing additional printing at low cost.

Figure 1:
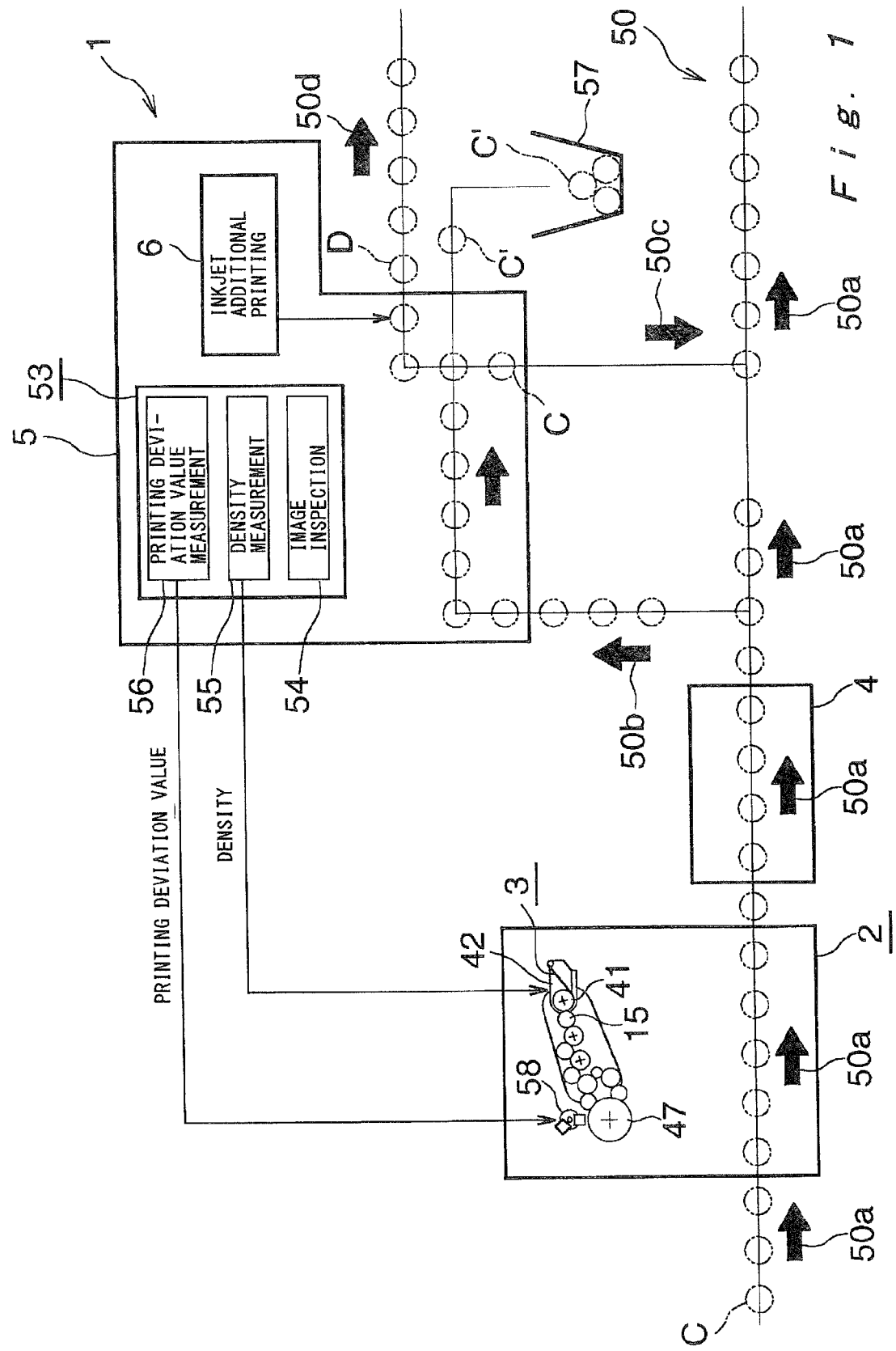
FIG. 1 is a block diagram showing a printing apparatus having a can inspection machine according to the present invention.

REFERENCE SIGNS LIST (1) can printing apparatus
(2) main printer
(5) can inspection machine
(6) secondary printer
(6a) head
(47) plate cylinder
(51) can rotation device
(52) can imaging device
(53) image processing device
(79) first camera
(80) second camera

DESCRIPTION OF EMBODIMENTS

Hereinafter, embodiments of the present invention will be explained with reference to the drawings. In the following explanation, the right side in FIG. 3 and FIG. 4 (the lower side in FIG. 5) is regarded as the front, the left side in FIG. 3 and FIG. 4 (the upper side in FIG. 5) is regarded as the rear. Right and left seen from the front are regarded as the right and the left.

FIG. 1 shows a can printing apparatus (1) according to an embodiment of the present invention. The can printing apparatus (1) includes a main printer (2) which is a plate type and performs printing onto cans (C), a dryer (4) drying printing surfaces of the cans (C) after performing printing with plates, a can inspection machine (5) inspecting a printing state of the printing surfaces, a secondary printer (6) performing additional printing on the cans (C) after performing printing with plates by inkjet (plateless type) and a conveyance device (50) conveying the cans (C).

The main printer (2) prints information such as a product name, a company name, ingredients and a barcode on a cylindrical can body which opens to the top (the body of a two-piece can, this will be referred to merely as a "can (c)" below).

After the cans (C) are printed by the main printer (2), the cans (C) are conveyed to subsequent stages via the dryer (4). Part of many cans (C) passed through the dryer (4) receive inspection in the can inspection machine (5).

The conveyance device (50) includes a main line (50a) for feeding the cans (C) to the main printer (2) and conveying the printed cans (C) to subsequent stages, a sampling line (50b) for conveying part of many cans (C) passing through the dryer (4) to the can inspection machine (5), a returning line (50c) for returning cans (C) determined as non-defective products in the can inspection machine (5) and a secondary line (50d) for conveying cans (D) to which additional printing is performed by the secondary printer (6) in the line different from the main line (50a).

Figure 2:
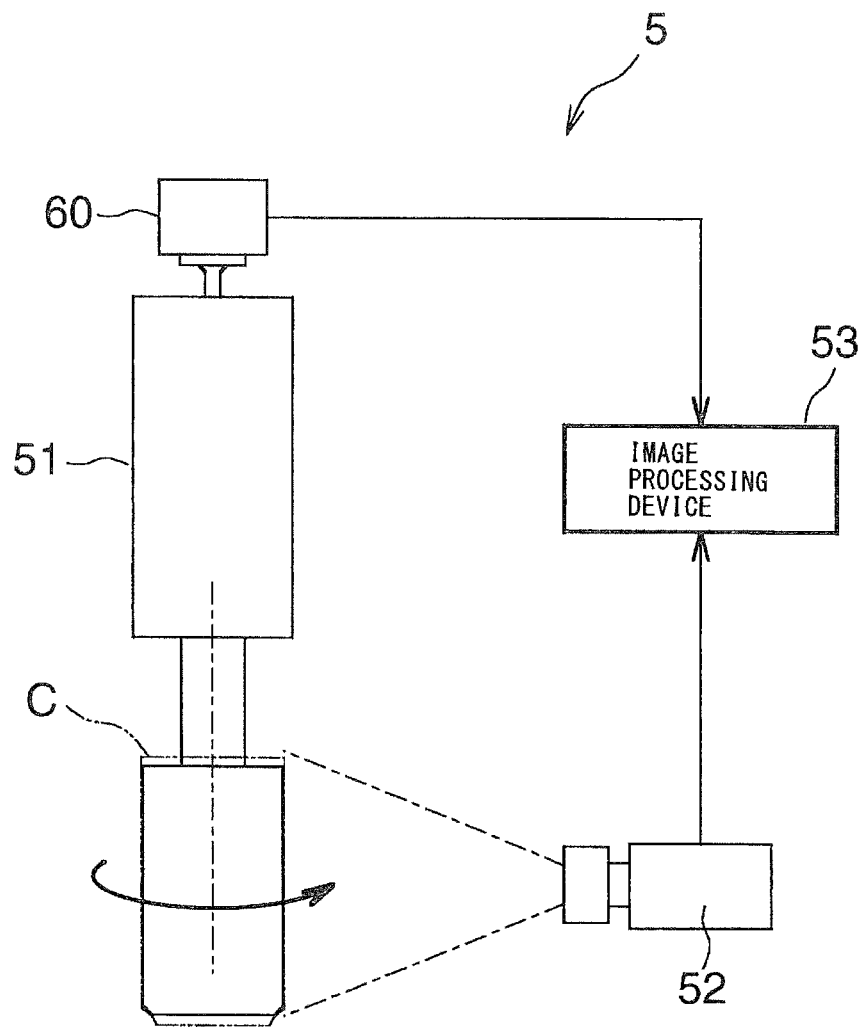
FIG. 2 is a view schematically showing an outline structure of the can inspection machine.

In the can inspection machine (5), the cans (C) are rotated by a can rotation device (51), and the can rotation device (51) on the drive side and the can (C) on the driven side are synchronized through an encoder (60), then, an image is taken by a can imaging device (52) and the image is processed in an image processing device (53) as schematically shown in FIG. 2.

The can inspection machine (5) is provided with an image inspection means (54), a density measurement means (55) and a printing deviation value measurement means (56) as the image processing device (53) which processes taken images as shown in FIG. 1. The cans (C) determined as non-defective products in the can inspection machine (5) are returned to the main line (50a) as described above, and cans (C') determined as inspection rejected products in the inspection machine (5) are discharged to an inspection rejected product storage (57).

Densities obtained in the density measurement means (55) and printing deviation values obtained in printing deviation value measurement means (56) in the can inspection machine (5) are fed back to the main printer (2). In the main printer (2), an ink supply amount is adjusted by a controller (34) so as to correspond to the density. Specifically, a corresponding contact length between an ink transfer roller (15) and an inkwell roller (41) is adjusted in each color based on each density value outputted from the density measurement means (55). Concerning the printing deviation value, a position of a plate cylinder (47) is adjusted by an automatic registering device (58).

Figure 3:
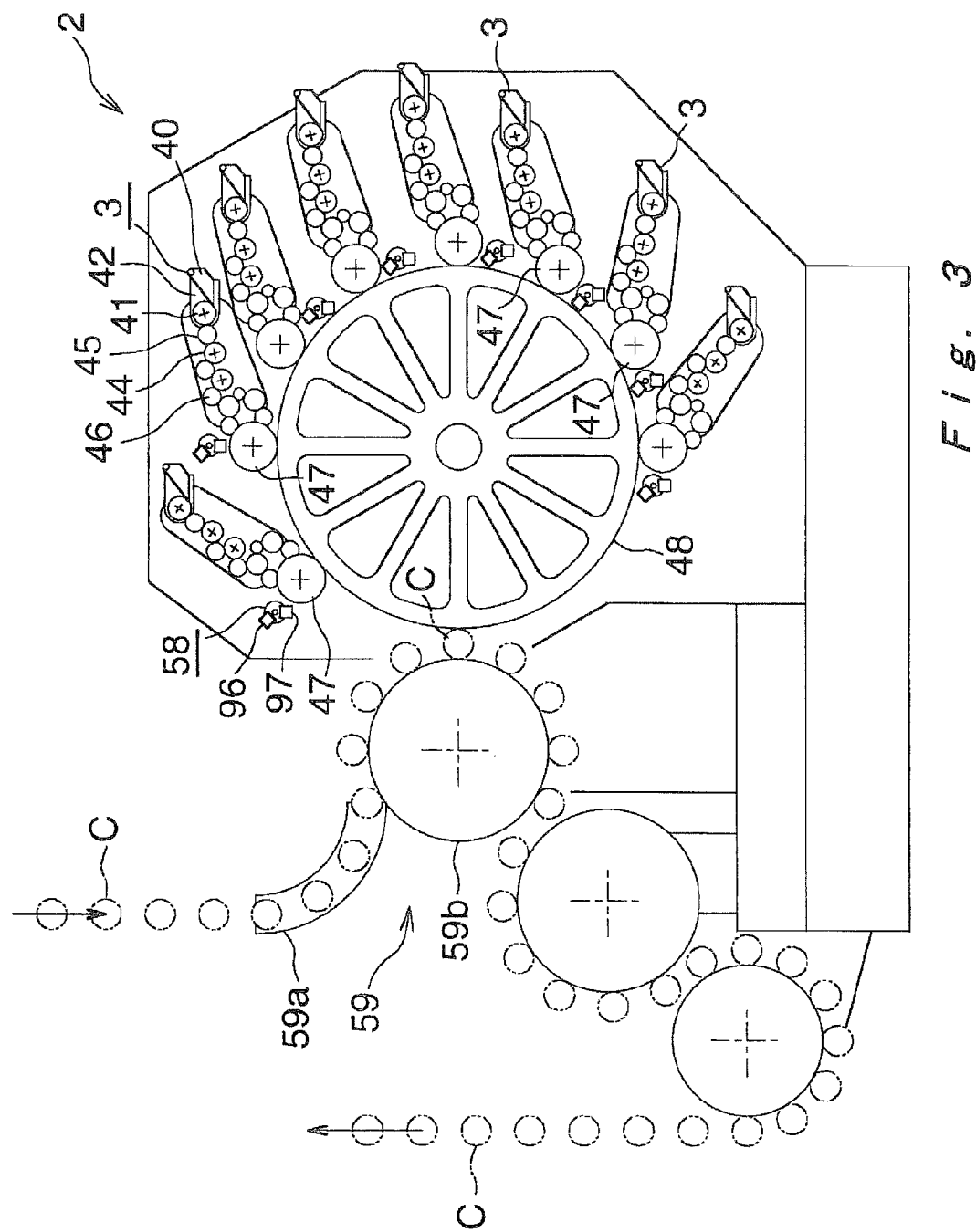
FIG. 3 is a side view showing a main printer.

The main printer (2) includes a plurality of (eight in the drawing) plate cylinders (47) having plates for printing different colors respectively, a blanket cylinder (48) performing printing on cans by inks transferred from the plate cylinders (47), ink supply devices (3) for supplying inks to respective plate cylinders (47), the registering device (58) performing position adjustment of plate cylinders and a can feeding device (59) configured by plural can feeding rollers (59a) and can feeding chute (59b) as shown in FIG. 3.

Figure 4:
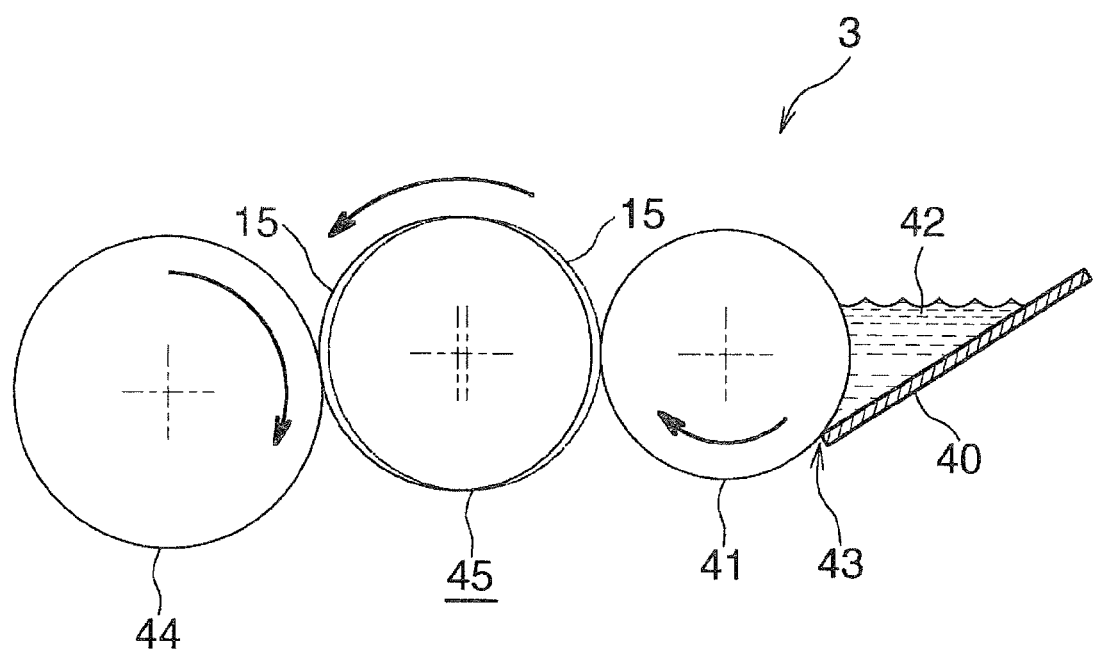
FIG. 4 is a schematic side view of a primary part of an ink supply device of the main printer.

As shown in FIG. 4 in an enlarged manner, the inkwell roller (41) is arranged close to a rear end portion of an inkwell member (40), which configure an inkwell (42), and an ink passage (43) with a given gap is formed between the rear end portion of the inkwell member (40) and a front surface of the inkwell roller (41) in the ink supply device (3).

Figure 5:
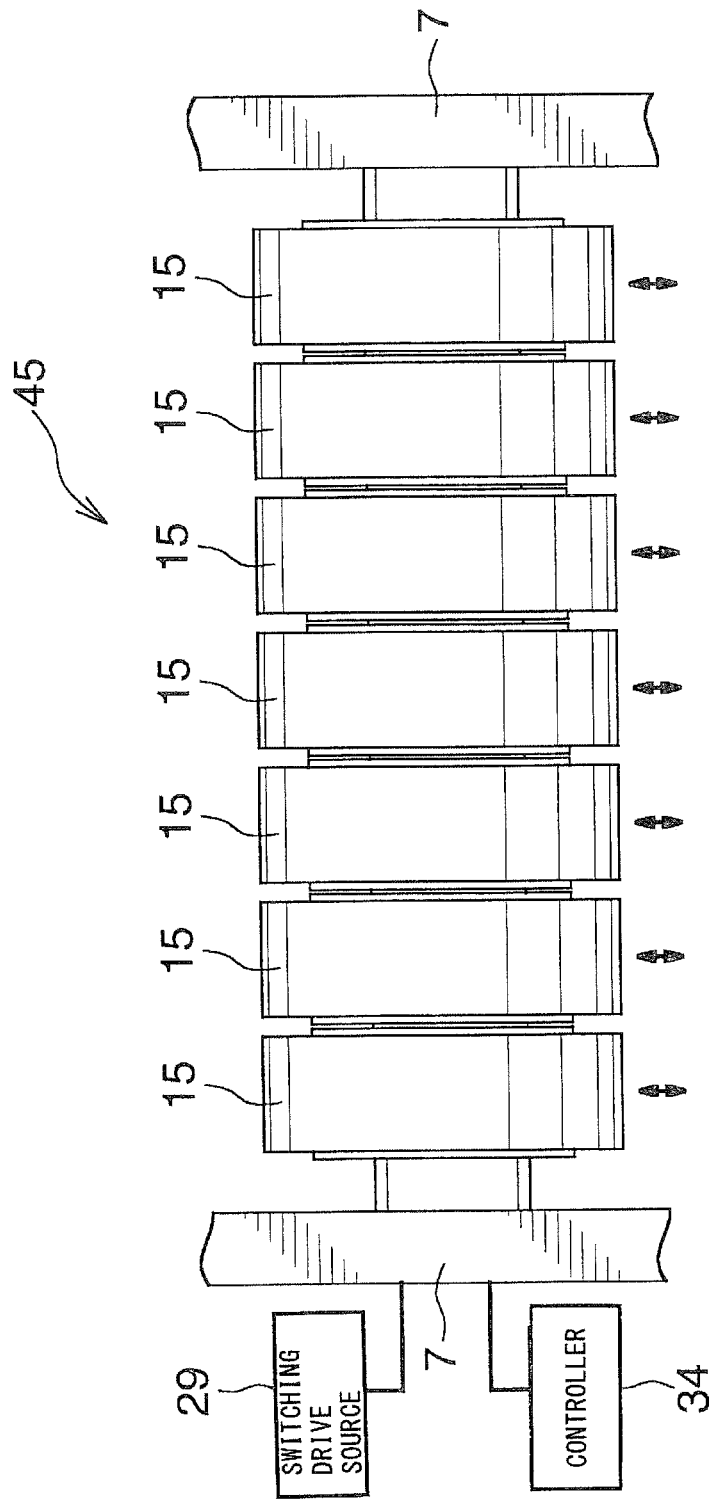
FIG. 5 is a plan view of an ink transfer roller unit of FIG. 4.

A first ink distributing roller (44) in plural ink distributing rollers (44) and (46) is arranged behind the inkwell roller (41), and an ink transfer roller unit (45) is arranged between the inkwell roller (41) and the ink distributing roller (44) so as to be close to the both. The roller unit (45) is an assembly of plural (seven in the drawing) ink transfer rollers (15) divided in an axial direction of the rollers (41) and (44), and these ink transfer rollers (15) are arranged at small intervals in the axial direction as shown in FIG. 5. Axes of these rollers (15), (41) and (44) are parallel to one another, extending in a right and left direction. The inkwell roller (41) and the ink distributing roller (44) are rotatably supported by a frame (7) of the main printer, which are continuously rotated by a not-shown drive device in arrow directions in FIG. 4 at given rotation speeds in synchronization with each other. For example, the rotation speed of the inkwell roller (41) is approximately 1/10 of that of the ink distributing roller (44).

The ink transfer roller (15) is switched between a rear end position (non-transfer position) where the ink transfer roller (15) is separated from the inkwell roller (41) and presses against the ink distributing roller (44) by a compressed air source (switching drive source) (29) and a front end position (transfer position) separated from the ink distributing roller (44) and presses against the inkwell roller (41).

The roller unit (45) is connected to the controller (34) which controls switching of positions by respective ink transfer roller (15). The controller (34) controls the ratio of respective transfer rollers (15) switched to the transfer position, thereby adjusting the ink amount supplied to a printing surface by the position in a width direction. As all the transfer rollers (15) of the roller unit (45) rotate at the same rotation speed, the ink amount supplied to the printing surface can be accurately controlled to a desired value by each transfer roller (15), namely, by the position of the printing surface in the width direction only by controlling the ratio of respective transfer rollers (15) switched to the transfer position.

Specific structures of mechanical parts of the can inspection machine (5) according to the embodiment of the present invention will be shown in FIG. 6 to FIG. 9.

The can inspection machine (5) includes a loading conveyor (61) sequentially loading cans (C) for inspection, a take-out device (62) provided at an end portion of the loading conveyor (61) and taking out the cans (C) for inspection from the loading conveyor (61), a can rotation device (51) holding and rotating the cans (C) for inspection taken out by the take-out device (62), a can imaging device (52) taking images of the cans (C), a control unit (not shown) configured by a computer including a CPU for executing logical operation of the image processing device (53), a ROM for storing control programs, a RAM for storing data and so on, a display for displaying image processing results and the like, an inspected non-defective product can unloading conveyor (63) for unloading non-defective cans (C) and a printing-defect cans discharge chute (64) for discharging cans (C') as inspection rejected products.

The take-out device (62) includes an adsorption part (65) for adsorbing the cans conveyed by the loading conveyor (61) and pushed out and a cylinder part (66) for allowing the adsorption part (65) to move upward. The adsorption part (65) has a semicylindrical concave portion (65a) to which a middle part of the can (C) is fitted.

The can rotation device (51) includes a main shaft (71) rotated by a motor (72) and a rotating disk (73) attached to the main shaft (71). The motor (72) is attached to an upper surface of a top wall of a housing (70), and the main shaft (71) is rotatably supported at the top wall of the housing (70).

The rotating disk (73) is concentric with the main shaft (71) and rotates integrally with the main shaft (71). On an outer periphery of the rotating disk (73), plural arms (73a) are provided at equal intervals so as to protrude outward in a radial direction. Vertical driven-side rotation shafts (74) are rotatably supported in respective arms (73a) of the rotating disk (73). Holding members (75) formed concentrically with the driven-side rotation shafts (74) and adsorbing/holding the cans (C) are attached to the driven-side rotation shaft (74).

The driven-side rotation shaft (74) revolves around the main shaft (71) with the rotation of the rotating disk (73). Via a set position of the take-out device (62), a set position of the can imaging device (52), a set position of unloading conveyor (63) and a set position of the discharge chute (64), the driven-side rotation shaft (74) returns to the set position of the take-out device (62).

On the upper side of the driven-side rotation shaft (74) positioned in the set position of the can imaging device (52), a drive device (76) rotating (revolving) the driven-side rotation shafts (74) is arranged and supported on the top wall of the housing (70). The drive device (76) includes a vertical drive-side rotation shaft (77) and a motor (78) provided concentrically with the drive-side rotation shaft (77).

As the can imaging device (52), a first camera (79) for imaging the entire can and a second camera (80) for imaging an end portion of an opening side of the can are used. Images taken by the first camera (79) are used by the image inspection means (54) and the density measurement means (55). Images taken by the second camera (80) are used by the printing deviation value means (56).

In the set position of the can imaging device (52), the drive-side rotation shaft (77) is opposite to the driven-side rotation shafts (74) in the axial direction, and magnets (81) and (82) exerting the attraction force to each other are fixed in a lower end of the drive-side rotation shaft (77) and in an upper end of the driven-side rotation shaft (74).

Accordingly, a lower surface of the magnet (81) provided in the lower end of the drive-side rotation shaft (77) and an upper surface of the magnet (82) provided in the upper end of the driven-side rotation shaft (74) are adsorbed (integrated) by the attraction force of the magnets (81) and (82) exerted therebetween.

Each driven-side rotation shaft (74) is supported by a cylindrical casing (83) provided in respective arms (73a) of the rotating disk (73) so as to rotate as well as so as not to move in the axial direction.

Figure 9:
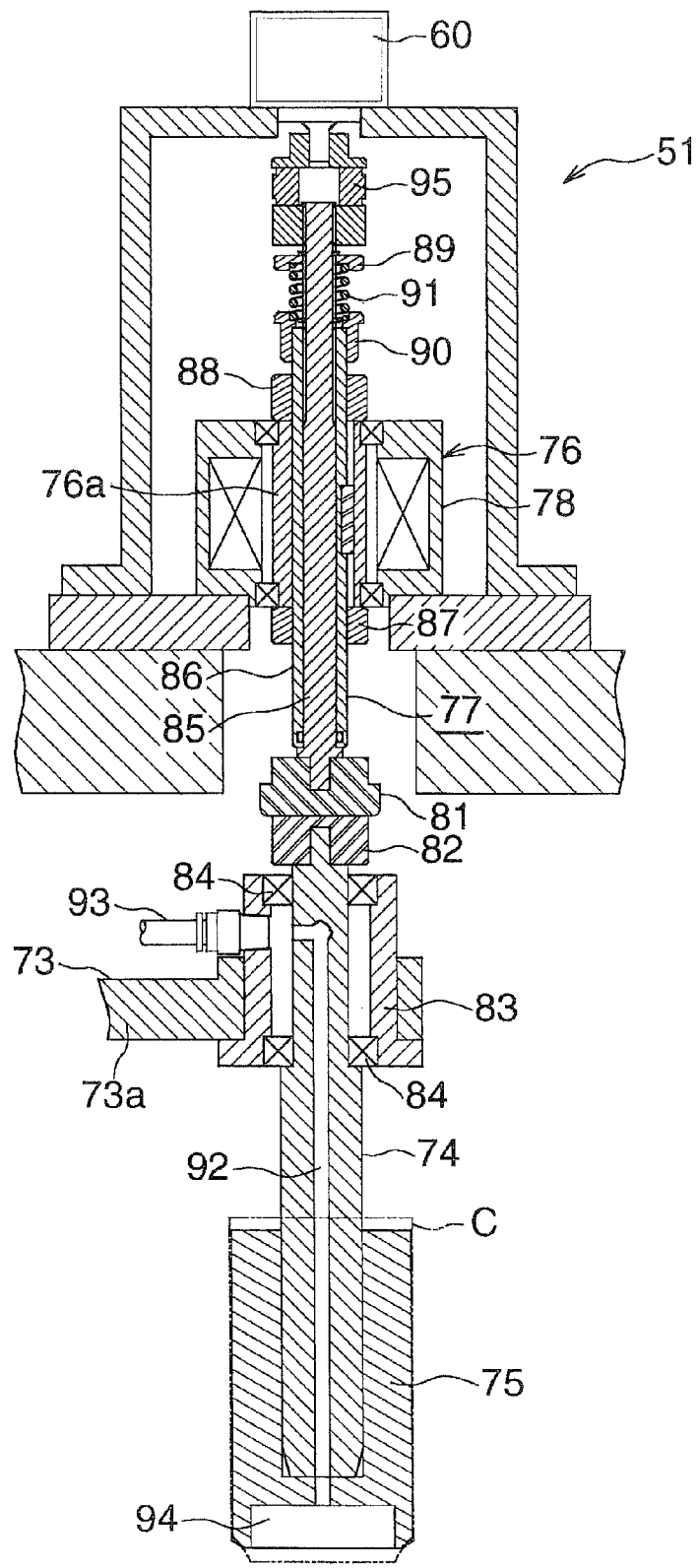
FIG. 9 is a vertical cross-sectional view showing a can rotation device of the can inspection machine.

As shown in FIG. 9, the drive-side rotation shaft (77) includes a solid shaft portion (85) and an outer cylinder portion (86) which is spline-coupled to the shaft portion (85) in a concentric manner. A lower end portion of the shaft portion (85) slightly protrudes downward from a lower end of the outer cylinder portion (86), and the magnet (81) is attached to the lower end portion of the shaft portion (85). An upper part of the shaft portion (85) protrudes upward from an upper end of the outer cylinder portion (86), and the rotary encoder (60) which detects the number of rotations (rotation angle) of the drive-side rotation shaft (77) is attached to an upper end of the shaft portion (85) through a coupling (95).

Male threads are provided on an outer periphery of the outer cylinder portion (86). A screw (87) screwed to a lower part of the outer cylinder portion (86) and a screw (88) screwed to an upper part of the outer cylinder portion (86) sandwich a motor rotor (76a) arranged on an outer periphery of the outer cylinder portion (86) from upper and lower both sides, thereby rotating the outer cylinder portion (86) together with the motor rotor (76a). Consequently, the shaft portion (85) spline-coupled to the outer cylinder portion (86) also rotates together. The shaft portion (85) can relatively move with respect to the outer cylinder portion (86) in the axial direction.

The driven-side rotation shaft (74) is supported by the casing (83) through a bearing (84). The drive-side rotation shaft (77) and the driven-side rotation shaft (74) are coupled (adsorbed) by the attraction force between the magnets (81) and (82), and the driven-side rotation shaft (74) rotates integrally with the rotation of the drive-side rotation shaft (77).

Ring-shaped spring receiving portions (89) and (90) are respectively fixed to an upper end portion of the shaft portion (85) and an upper end portion of the outer cylinder portion (86) of the drive-side rotation shaft (77), and a compressed coil spring (91) is arranged between the both spring receiving portions (89) and (90). Therefore, when the shaft portion (85) moves downward, the compressed coil spring (91) is further compressed and biases the shaft portion (85) upward, thereby preventing movement of the shaft portion (85) in a lower direction. Accordingly, the magnets (81) and (82) exerting the attraction force to each other do not contact each other, and abrasion between the magnets (81) and (82) can be prevented.

The drive-side rotation shaft (77) rotates by being driven by the motor (78) and the can (C) held by the driven-side rotation shaft (74) rotates with the above rotation, then, an image of one rotation is taken by the can imaging device (52). At this time, time for one pixel is determined so as to correspond to an output of the rotary encoder (60) for eliminating an error.

The rotation of the can (C) and the rotation of the rotary encoder (60) (the rotation of the drive-side rotation shaft (77)) are synchronized with each other to eliminate an error. Accordingly, even when an output (pulse) of the rotary encoder (60) is synchronized with the flow of one pixel in the image and rotation unevenness occurs in respective cans (C) to be measured, taken images of respective cans are not stretched or contracted, and stable inspection can be performed.

The driven-side rotation shaft (74) is provided with an air vent passage (92) one end of which opens to a lower end and the other end of which opens to an outer periphery near an upper end portion. A pipe for vacuum drawing for performing vacuum drawing (93) of the air vent passage (92) is attached to the casing (83).

The holding member (75) is made of resin and having a cylindrical shape. In a lower end portion of the holding member (75), a cylindrical suction chamber (94) opening downward is provided. The air vent passage (92) of the driven-side rotation shaft (74) communicates with the suction chamber (94). When vacuum drawing is performed by a not-shown vacuum pump through the pipe for vacuum drawing (93), the suction chamber (94) is in a negative pressure (vacuum) and the can (C) is adsorbed and held by the holding member (75).

In the can inspection machine (5), the image on the printing surface of the can (C) is started to be taken from an arbitrary position of the can (C) in a state where the can (C) rotates at arbitrary speed.

When a printing end position matches a printing start position in the printing of one rotation, the printing of just one rotation is completed. The printing is slightly deviated by each can in a matching position between the printing end position and the printing start position, therefore, large deviation occurs in each can in the case where the matching position is in an intermediate part of the image taking. If the printing from a designated mark to a designated mark is regarded as one rotation, the matching position of the printing is included in the intermediate part, which is not preferable. Accordingly, the image of one rotation starting from the printing start position to the printing end position is taken at the time of taking the image. As the designated mark, a mark which can be easily found in the printed images, for example, bar codes are used.

As the position of the can (C) conveyed to the can inspection machine (5) is not prescribed, positions of the can (C) facing the cameras (79) and (80) are random. Therefore, it is necessary to find the printing start position for taking the image of one rotation. In the image taking operation, distances (angles) from a designated mark (M) to printing start positions (S1) and (S2) are known in advance in FIG. 10, therefore, the designated mark (M) is found first. After the designated mark is found, a position moved in a reverse direction by "a" corresponding to the angle is preferably determined as the printing start position (S1), namely, an image taking start position. It is also preferable that a position moved in a positive direction by "b" is determined as the printing start position (S2), namely, the image taking start position. Accordingly, the image of just one rotation, which is from the printing start positions (S1)/(S2) to the printing end positions (E1)/(E2) which is shown by L1 or L2 can be taken.

The image inspection by the image inspection means (54) of the can inspection machine (5) has been performed from the past, in which a master image and a taken image are compared pixel by pixel using the image inspection means (54), and a partial lack in the image, stains by ink scattering and so on are inspected. In the image inspection means (54), defects exceeding a prescribed size are regarded as inspection rejected products, and defects exceeding a deviation tolerance with respect to the master image are also regarded as inspection rejected products.

The inspection by density measurement means (55) is performed with respect to monochrome solid portions. That is, it is difficult to measure the density in places where plural colors overlap, therefore, places including monochrome solid portions are designated in respective colors, and densities in the designated places (density measurement places) are measured. A density value can be calculated as an arithmetic mean value of RGB components of pixels designated as the density measurement place, and can be obtained as a density difference with respect to the density of the master image in each place. The density can be measured as long as the monochrome solid portion has a size of, for example, 0.8 mm×0.8 mm. In the case where it is difficult to measure the accurate density because the size is not capable of being secured, only whether the density difference with respect to the master image is within a reference or not is determined. Densities corresponding to the number (seven) of the ink transfer rollers (15) can be obtained with respect to one color. The number of colors (the number of plate cylinders) is eight in the embodiment, therefore, density measurement values of 8×7 can be obtained. The density measurement results are displayed on the display of the can inspection machine (5). The density measurement results are fed back to the main printer (2), thereby controlling positions of respective ink transfer rollers (15) by the controller (34) of the ink supply device (3) to change the ink amounts to be supplied. Accordingly, the density is corrected before a density defective product is produced, thereby maintaining good printing state in the main printer (2).

The above image inspection means (54) and the density measurement means (55) are performed by using the image of the entire can taken by the first camera (79), while the printing deviation value means (56) is performed by using the image obtained by the second camera (80) which takes the end portion of the opening side of the can.

The end portion of the opening side of the can (C) is a portion to be covered with a lid, which is a place where the printing is not performed and the inspection is not required in the conventional cans. In the cans (C) inspected by the can inspection machine (5) according to the embodiment, marks for inspecting printing deviation values are printed for respective colors. That is, as shown in FIG. 11(a), on the printing surface of the can (c), marks for inspecting printing deviation values shown by "A" are added in addition to items existing from the past such as a product name, a company name, ingredients and a bar code.

Figure 11:
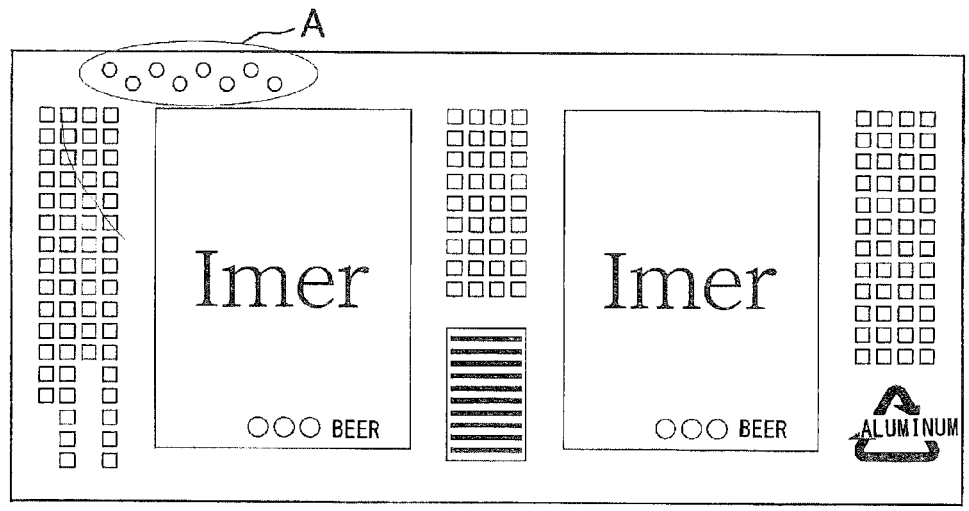
FIGS. 11(a) and 11(b) are views showing printing deviation obtained by the can inspection machine.
Figure 11:
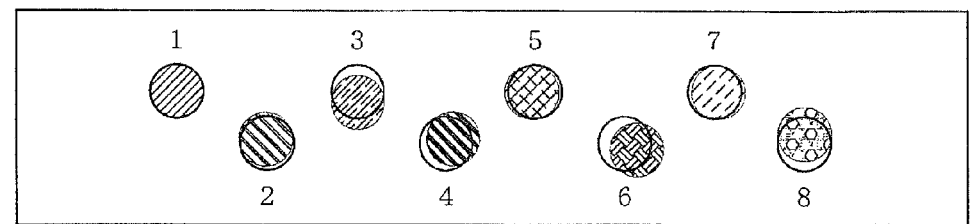
Figure 12:
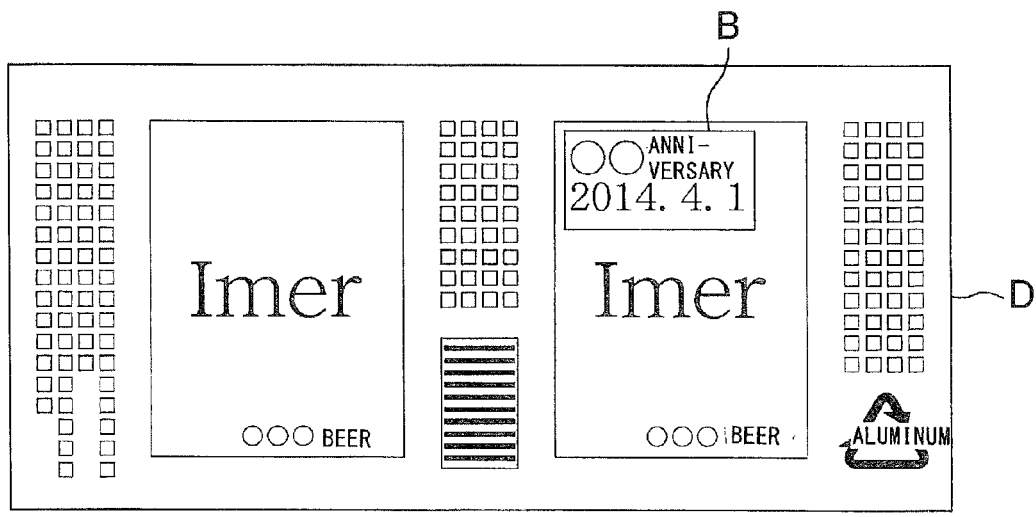
FIG. 12 is a view showing an example of a side surface of a can to which additional printing is performed.

The marks for inspecting printing deviation values (A) have eight colors in total from one to eight as shown in an enlarged manner in FIG. 11(b). Positions shown by solid lines in the drawing are reference positions (positions of designated marks in the master image), and positions shown by chain double dashed lines in the drawing are positions of respective colors obtained from the taken image. According to the drawing, it is found that, for example, printing deviation is extremely small in a color of No. 7, a printing deviation value in a height direction of the can (C) is high in a color of No. 3 and a printing deviation value in a circumferential direction of the can (C) is high in a color of No. 6. The printing deviation value is calculated as a value indicating by how many pixels (or to what degree (mm)) the position of the designated mark in the master image is deviated from the position of the designated mark in the taken image, and a numeral value is displayed on the display of the can inspection machine (5). Deviation amounts are calculated concerning the can height direction (the axial direction of the plate cylinder (47)) and the can circumferential direction (the circumferential direction of the plate cylinder (47)) respectively. The printing deviation value measurement results can be fed back to the main printer (2) manually as well as automatically.

The registering device (58) includes a first rotation drive device (96) moving the plate cylinder (47) in the axial direction of the plate cylinder (47) and a second rotation drive device (97) moving the plate cylinder (47) in a circumferential direction of the plate cylinder (47) as shown in FIG. 3. The explanation of the detailed structure of respective rotation drive devices (96) and (97) is omitted. The printing deviation values obtained by the printing deviation value means (56) of the can inspection machine (5) are fed back to the respective rotation drive devices (96) and (97), and when the printing deviation value exceeds the prescribed size, the position of the plate cylinder (47) is corrected by the respective rotation drive devices (96) and (97).

As the printing deviation values (positional deviations of the plate cylinders of the main printer (2)) can be corrected (registered) before a density defective product is produced, the good printing state can be maintained.

The secondary printer (6) includes a printing head (6a) and a processing unit (not shown) which gives an instruction of printing to the printing head (6a) based on a predetermined printing pattern and processing data of the image processing device (53).

Figure 6:
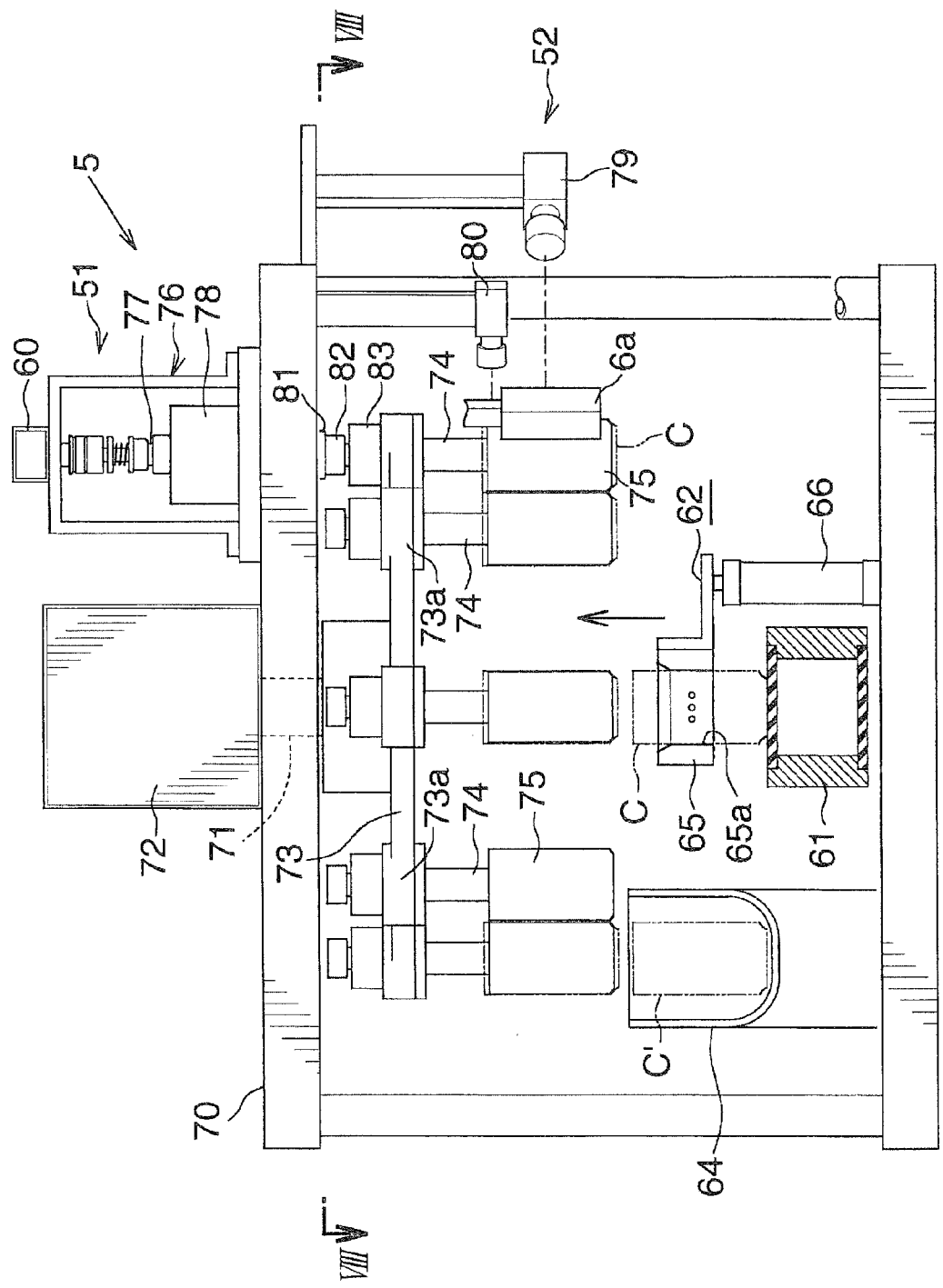
FIG. 6 is a front view of the can inspection machine.
Figure 7:
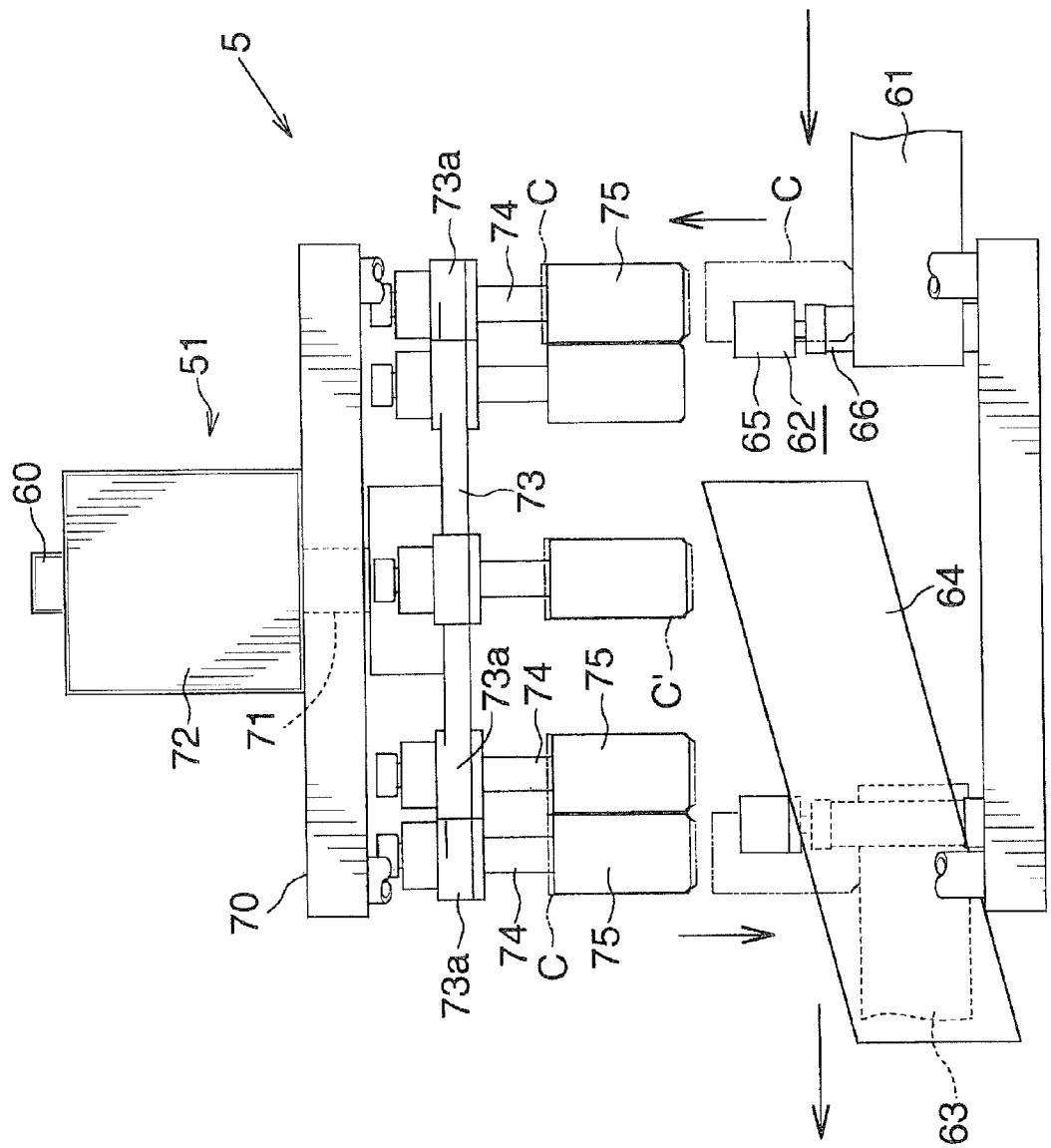
FIG. 7 is a side view of FIG. 6.
Figure 8:
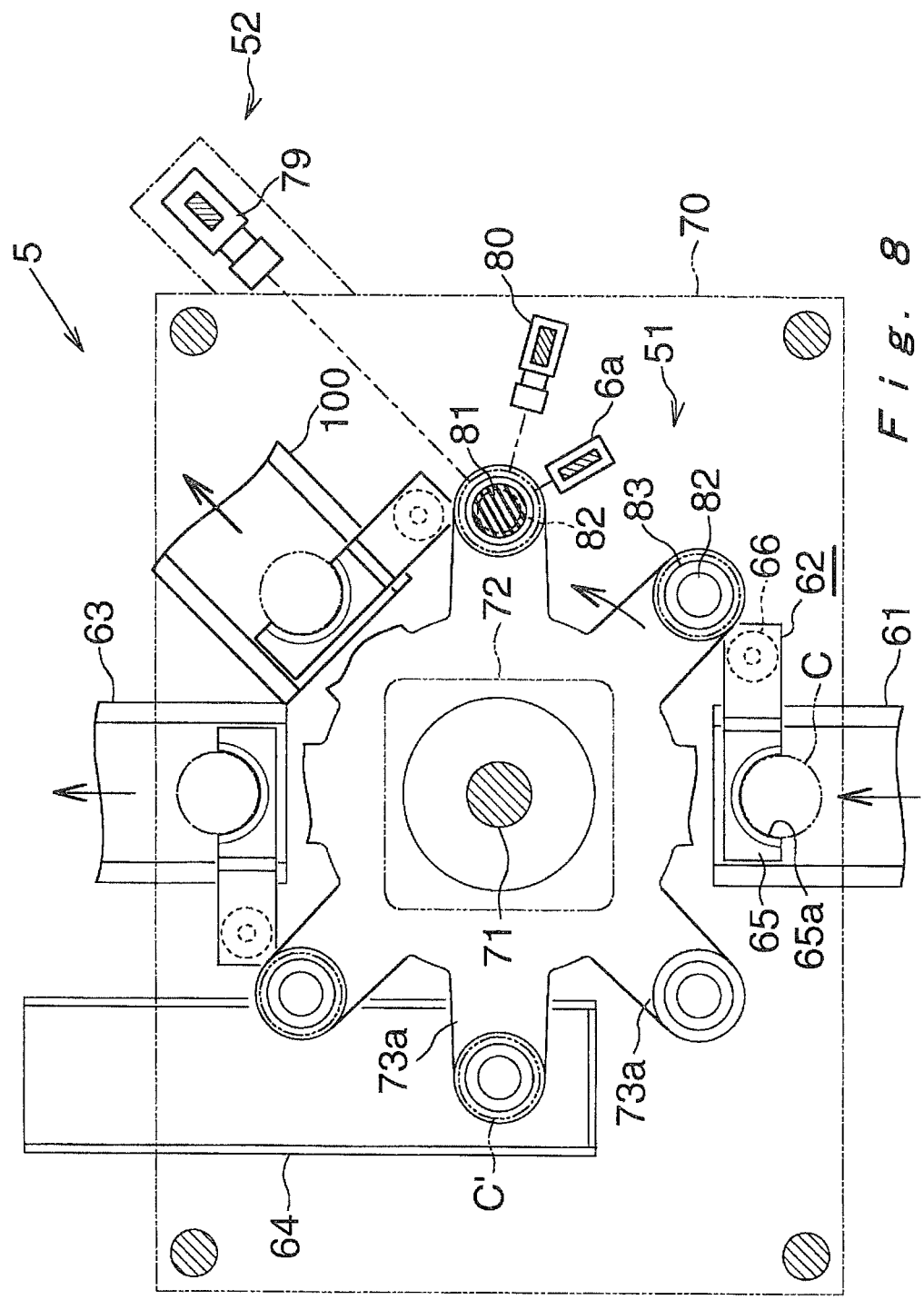
FIG. 8 is a cross-sectional view taken along VIII-VIII line of FIG. 6.

The printing head (6a) is arranged so as to face the can (C) held by the can rotation device (51) of the can inspection machine (5) as shown in FIG. 6 and FIG. 8. The processing unit is formed by adding a program for inkjet printing to the controller of the can inspection machine (5).

The can inspection machine (5) is provided with an additional printing can unloading conveyor (100) for unloading cans (D) obtained after additional printing to the secondary line (50d) in addition to the printing head (6a).

The inkjet printing by the secondary printer (6) is performed by using the can inspection machine (5) during a period when the inspection using the can inspection machine (5) is not performed. That is, it is sufficient that the inspection of the printing state by the can inspection machine (5) is performed by sampling, therefore, idle time is generated between inspections. Moreover, there is a small quantity of cans (C) to which the additional printing is performed, therefore, the additional printing to a necessary quantity of cans (C) can be performed by using the idle time of inspections.

As the printing by inkjet is a plateless type, an arbitrary pattern including pictures can be used as the printing pattern. For example, a pattern desired by a purchaser can be added in accordance with applications such as wedding and various anniversaries in a style of, for example, "anniversary of something+date". An added value can be given to the design of the can (D) in this manner.

In the inkjet printing which has been performed from the past, an expiration date and so on are printed on a bottom of the can (C). In such inkjet printing, it is not necessary to specify a position on the bottom as the bottom of the can (C) is plain. However, the above-described additional printing is required to be performed on a side surface of the can (C), and it is not adequate to perform the additional printing on an important pattern such as the product name which has been already printed on the side surface of the can (C). Therefore, it is important to identify the position where the additional printing is performed.

Figure 10:
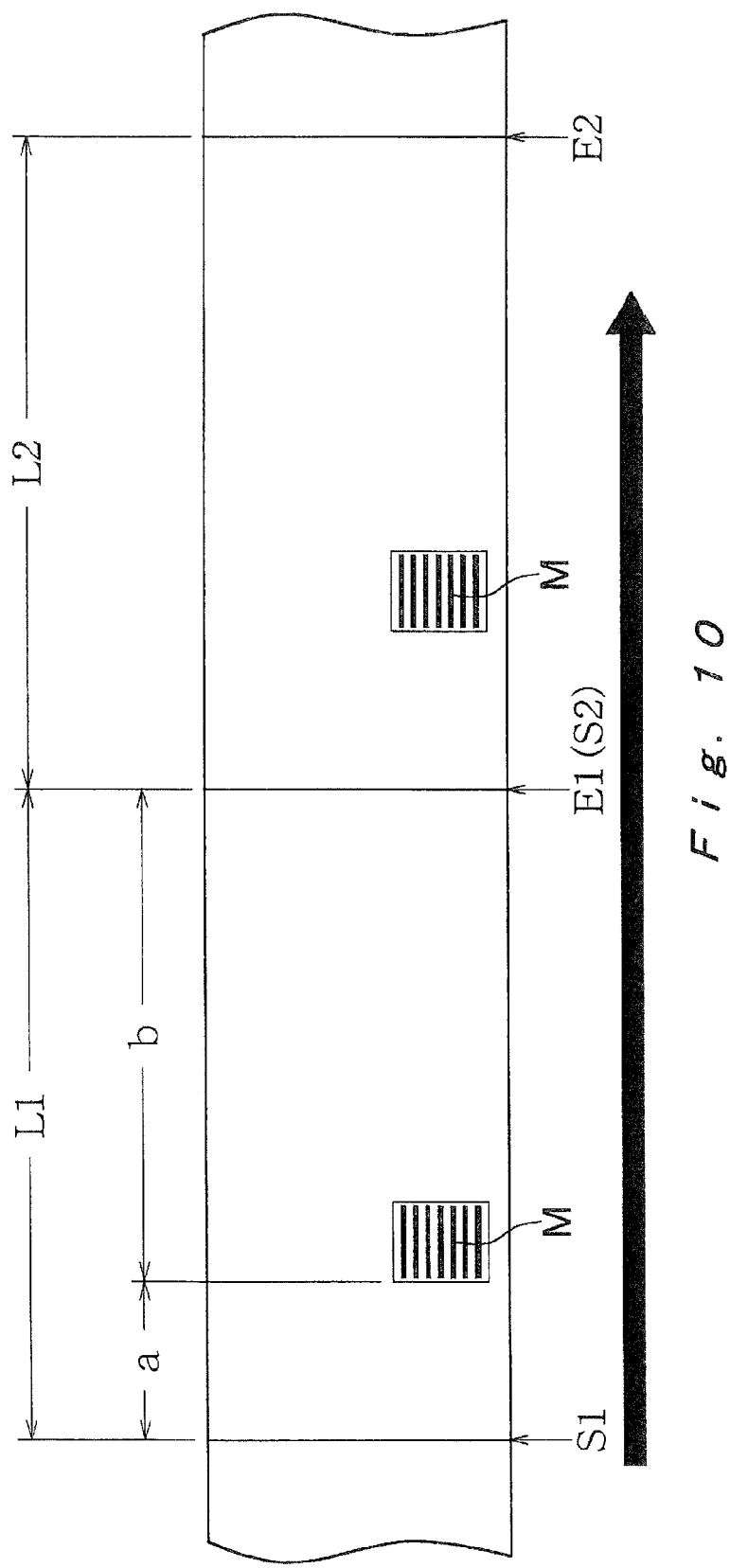
FIG. 10 is a view schematically show steps of taking an image by the can inspection machine.

According to the above can inspection machine (5), printing start positions (S1) and (S2) are specified as explained with reference to FIG. 10, therefore, it becomes easy to allow the head (6a) of inkjet to face a necessary position (a position where the pattern already printed does not adversely affected even after the additional printing is performed) of the can (C) by relatively rotating the secondary printer (6) and the can (C).

In FIG. 6 and FIG. 8, the head (6a) of inkjet faces the side surface of the can (C) in the stopped state, and ink is injected from the head (6a) so as to correspond to the rotation angle of the can (C) when the can (C) is rotated. That is, the can rotation device (51), the can imaging device (52) and the image processing device (53) of the can inspecting machine (5) are used for the printing by the secondary printer (6).

The cans (C) requiring the additional printing are loaded into the can inspection machine (5) by the sampling line (50b) of the conveyance device (50) and rotated as shown in FIG. 2 in the same manner as the cans (C) for inspection. From what angle of a position from the printing start positions (S1) and (S2) the additional printing is started is previously set, and the additional printing by the secondary printer (6) is started during one rotation of the can (C) after the printing start positions (S1) and (S2) are specified.

The printing start positions (S1) and (S2) necessary for inspection are specified with extremely high accuracy as described above, and the position to which the additional printing is performed by the secondary printer (6) is determined with high accuracy accordingly.

The cans (D) obtained after the additional printing is performed are unloaded by the additional printing can unloading conveyor (100) and the secondary line (50d) which are different from the inspected non-defective product can unloading conveyor (63) and the returning line (50c).

In order to perform adequate additional printing to the cans (C) obtained after the plate printing is performed, the rotation device of cans, the image processing device and so on are necessary and the cost is increased. According to the above can printing apparatus (1), benefits by the unmanned operation using the can inspection machine (5) can be obtained as well as costs necessary for additional printing is suppressed to be extremely low as the can inspection machine (5) is used for performing the additional printing, as a result, both the inspection of printing to the cans (C) and the additional printing to the cans (C) can be performed.

In the above description, automatic conveyance using the conveyance device (50) is explained, however, the conveyance and the loading to the can inspection machine (5) may partially include manual operation, not limited to the automatic operation. That is, the minimum configuration of the can inspection machine (5) includes the can rotation device for rotating cans, the can imaging device for taking images of side surfaces of cans and the image processing device for processing the taken images, to which the printing head (6a) and the processing unit are added.

INDUSTRIAL APPLICABILITY

The printing accuracy of the main printer is improved by the can inspection machine which inspects the printing state as well as additional printing can be performed at low cost by performing additional printing using the can rotation device and the image processing device of the can inspection machine, which can contribute to improvement in cost performance of the can printing apparatus.

The invention claimed is:

1. A can printing apparatus comprising:
   a main printer having plural plate cylinders for printing different colors and performing printing onto side surfaces of cans;
   a can inspection machine inspecting a printing state; and
   a secondary printer performing additional printing to the side surfaces of the cans after the printing by the main printer,
   wherein the can inspection machine includes
       a can rotation device which rotates cans,
       a can imaging device which takes images of the side surfaces of the cans, and
       an image processing device which processes the taken images,
   wherein the secondary printer includes
       a printing head which faces a side surface of a can held by the can rotation device of the can inspection machine and
       a processing unit which gives an instruction of printing to the printing head based on a predetermined printing pattern and processing data of the image processing device of the can inspection machine,
   wherein the can imaging device includes a first camera for taking an image of the entire can, and
   wherein the image processing device includes
       an image inspection means for inspecting whether the image is correctly printed as compared with a master image by using the image taken by the first camera, and
       a density measurement means for measuring densities in positions designated by respective colors by using the image taken by the first camera.

2. The can printing apparatus according to claim 1,
   wherein the can imaging device includes a second camera for taking an image of an end portion of an opening side of the can, and
   wherein the image processing device includes
       a printing deviation value measurement means for measuring deviation values with respect to set positions of marks for inspecting printing deviation printed on the end portion of the opening side of the can for respective colors by using the image taken by the second camera.

3. A can printing apparatus comprising:
a main printer having plural plate cylinders for printing different colors and performing printing onto side surfaces of cans;
a can inspection machine inspecting a printing state; and
a secondary printer performing additional printing to the side surfaces of the cans after the printing by the main printer,
wherein the can inspection machine includes
a can rotation device which rotates cans,
a can imaging device which takes images of the side surfaces of the cans, and
an image processing device which processes the taken images,
wherein the secondary printer includes
a printing head which faces a side surface of a can held by the can rotation device of the can inspection machine and
a processing unit which gives an instruction of printing to the printing head based on a predetermined printing pattern and processing data of the image processing device of the can inspection machine,
wherein a designated mark and an angle from the designated mark to an image taking start position is previously set in the can imaging device, and
wherein the can imaging device is configured to perform an image taking operation that takes an image of one rotation from the image taking start position found using the designated mark as a reference.

* * * * *